United States Patent
Renz et al.

(10) Patent No.: US 7,150,346 B2
(45) Date of Patent: *Dec. 19, 2006

(54) BAG SYSTEM

(75) Inventors: Charles J. Renz, Briarcliff Manor, NY (US); Chariklia Varellas, Whitestone, NY (US)

(73) Assignee: Playtex Products, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/890,448

(22) Filed: Jul. 13, 2004

(65) Prior Publication Data

US 2004/0245127 A1 Dec. 9, 2004

Related U.S. Application Data

(63) Continuation of application No. 10/331,130, filed on Dec. 27, 2002, now Pat. No. 6,779,638.

(60) Provisional application No. 60/428,463, filed on Nov. 22, 2002, provisional application No. 60/403,415, filed on Aug. 14, 2002, provisional application No. 60/343,769, filed on Dec. 27, 2001.

(51) Int. Cl.
*A45C 3/00* (2006.01)
*A45C 3/06* (2006.01)

(52) U.S. Cl. .................. 190/111; 190/109; 190/110; 150/117; 383/38; 383/110

(58) Field of Classification Search .............. 150/117; 190/108–112; 383/38, 110, 117; 206/545
See application file for complete search history.

(56) References Cited

U.S. PATENT DOCUMENTS

| | | | | |
|---|---|---|---|---|
| 2,533,850 A * | 12/1950 | Syracuse | .................. | 150/117 |
| 2,584,435 A * | 2/1952 | Doerr | .......................... | 165/58 |
| 3,117,607 A * | 1/1964 | Siegel | ....................... | 150/117 |
| 3,759,356 A * | 9/1973 | Bostick et al. | ............. | 190/111 |
| 3,963,102 A * | 6/1976 | Carp | ........................... | 190/108 |
| 4,463,789 A * | 8/1984 | Leiserson | ................... | 383/97 |
| 4,609,084 A * | 9/1986 | Thomas | ..................... | 190/110 |
| 4,648,512 A * | 3/1987 | Tarozzi et al. | ............. | 206/542 |
| 4,961,522 A * | 10/1990 | Weber | ....................... | 224/585 |
| 5,230,450 A * | 7/1993 | Mahvi et al. | ............... | 224/153 |
| 5,649,658 A * | 7/1997 | Hoffman et al. | ........... | 224/576 |
| 5,762,170 A * | 6/1998 | Shyr et al. | .................. | 190/109 |
| 5,865,314 A * | 2/1999 | Jacober | ..................... | 206/570 |
| 5,911,262 A * | 6/1999 | Steinhart | ................... | 150/103 |
| 5,961,216 A * | 10/1999 | Quinn et al. | .................. | 383/4 |
| 6,230,952 B1* | 5/2001 | Jupiter | ...................... | 224/655 |
| 6,298,993 B1* | 10/2001 | Kalozdi | ..................... | 206/581 |
| 6,427,475 B1* | 8/2002 | DeFelice et al. | ........... | 62/457.2 |
| 6,575,273 B1* | 6/2003 | Bergkvist et al. | ........... | 190/114 |
| 6,779,638 B1* | 8/2004 | Renz et al. | .................. | 190/111 |
| 2002/0074259 A1* | 6/2002 | Gutierrez et al. | ........... | 206/545 |
| 2002/0170935 A1* | 11/2002 | Annis | .......................... | 224/653 |
| 2002/0193731 A1* | 12/2002 | Myers et al. | .................. | 604/74 |
| 2003/0024960 A1* | 2/2003 | Greenstein et al. | ......... | 224/153 |

FOREIGN PATENT DOCUMENTS

DE 3700105 A1 * 7/1988

(Continued)

*Primary Examiner*—Sue A. Weaver
(74) *Attorney, Agent, or Firm*—Ohlandt, Greeley, Ruggiero & Perle, L.L.P.

(57) ABSTRACT

A bag system for a breast pump system is provided. The bag system separates used and unused components of the breast pump system, provides thermal isolation for stored breast milk, and orientates the breast pump so that it is readily useable and accessible.

18 Claims, 16 Drawing Sheets

FOREIGN PATENT DOCUMENTS

| | | | | |
|---|---|---|---|---|
| DE | 3841362 | A1 | * | 6/1990 |
| FR | 2653312 | A3 | * | 4/1991 |
| GB | 2178401 | A | * | 2/1987 |
| JP | 08168408 | A | * | 7/1996 |
| JP | 408280432 | A | * | 10/1996 |
| JP | 09182610 | A | * | 7/1997 |
| JP | 0965929 | A | * | 9/1997 |
| WO | WO9321793 | | * | 11/1993 |
| WO | WO 97/05913 | | * | 2/1997 |

* cited by examiner

BAG SYSTEM

RELATED APPLICATION

This application is a continuation of and claims priority in, U.S. application Ser. No. 10/331,130, filed Dec. 27, 2002 now U.S. Pat. No. 6,779,638 B2, which claimed priority to U.S. Provisional Application Ser. No. 60/343,769, filed Dec. 27, 2001, U.S. Provisional Application Ser. No. 60/403,415, filed Aug. 14, 2002 and U.S. Provisional Application Ser. No. 60/428,463, filed Nov. 22, 2002, the disclosures of which are incorporated herein by reference.

BACKGROUND OF THE INVENTION

1. Field of the Invention

The present invention relates to apparatus and methods for obtaining breast milk. More particularly, the present invention relates to a bag system for a breast pump system.

2. Description of the Related Art

Bags for breast pump systems for obtaining breast milk are known. Such bags provide an inner volume for the various components of the breast pump system including the breast pump and breast cups. The conventional bag suffers from the drawback of failing to provide adequate thermal isolation for stored breast milk. The conventional bag further suffers from the drawback of exposing clean components to used components, which adds to the risk of contamination of the clean components.

SUMMARY OF THE INVENTION

It is an object of the present invention to provide a bag system for a breast pump system in which the breast pump is easily accessible and removable.

It is another object of the present invention to provide a bag system in which the breast pump may be operated while exposed or concealed.

It is a further object of the present invention to provide such a bag system that separates used and unused components of the breast pump system, provides thermal isolation for stored breast milk and/or orientates the breast pump so that it is readily useable and accessible.

It is yet another object of the present invention to provide such a bag system in which used components are isolated from clean components thereby preventing or ameliorating the possibility of contamination.

It is still another object of the present invention to provide such a bag system that provides thermal isolation for stored breast milk.

These and other objects and advantages of the present invention are provided by a bag for a breast pump that has a first compartment and a second compartment. The first compartment has a first volume, a plurality of first walls and a first closure and the second compartment has a second volume, a plurality of second walls and a second closure. The first walls and first closure are secured to each other to form the first compartment, and the second walls and second closure are secured to each other to form the second compartment. The second compartment is secured to at least one of the plurality of first walls, the second volume is in substantial isolation from the first volume, and the breast pump is disposed in the second volume.

The second closure can be a flap having an inside surface with the flap being pivotally connected to at least one of the plurality of first walls and the inside surface of the flap having a holding structure disposed thereon for removably holding the breast pump on the flap. One of the plurality of first walls can be a front wall having a bottom portion and another of the plurality of first walls can be a bottom wall. The flap can be pivotally connected to the bottom portion of the front wall so that the flap opens into a first position that is substantially adjacent to the bottom wall and substantially parallel with the bottom wall, and the holding structure retains the breast pump so that the breast pump is in an upright orientation when the flap is in the first position.

The holding structure can be VELCRO® secured to the inside surface of the front flap which corresponds to VELCRO® on the base of the breast pump. The holding structure can be substantially transparent. The holding structure can also be a mesh netting that is secured to the inside surface of the flap to form a pocket. The second compartment can further have an orifice that provides communication between the second volume and the first volume. One of the plurality of first walls can be a front wall with the second closure being a flap pivotally connected to the front wall, and the front wall and the flap being substantially disposed in a common plane or planar section.

The present invention also includes a bag system for a breast pump, breast cups and bottles. The bag system has an inner bag and an outer bag. The outer bag has a first compartment having a first volume defined by a plurality of first walls and a first closure, and a second compartment having a second volume defined by a plurality of second walls and a second closure. The second compartment can be secured to at least one of the plurality of first walls, the second volume can be in substantial isolation from the first volume, the breast pump can be disposed in the second volume, and the inner bag can be disposed in the first volume.

The second closure can be a flap having an inside surface with the flap being pivotally connected to at least one of the plurality of first walls and the inside surface of the flap having a holding structure disposed thereon for removably holding the breast pump on the flap. One of the plurality of first walls can be a front wall having a bottom portion and another of the plurality of first walls can be a bottom wall. The flap can be pivotally connected to the bottom portion of the front wall so that the flap opens into a first position that is substantially adjacent to the bottom wall and substantially parallel with the bottom wall, and the holding structure can retain the breast pump so that the breast pump is in an upright orientation when the flap is in the first position. The holding structure can secure the breast pump to the inside surface of the front flap by VELCRO®. The holding structure can be substantially transparent. The holding structure can also be a mesh netting that is secured to the inside surface of the flap to form a pocket.

The second compartment can further have an orifice that provides communication between the second volume and the first volume. One of the plurality of first walls can be a front wall, the second closure can be a flap pivotally connected to the front wall, and the front wall and the flap can be substantially disposed in a common plane or planar section. The inner bag can be a first inner bag, a second inner bag and a third inner bag. The third inner bag can be thermally insulated. The first compartment can have an inner surface with a fastening member disposed thereon and the fastening member can be removably securable to the inner bag to selectively retain the inner bag in the first volume. The first compartment can have an inner surface with a housing member disposed thereon, and the housing member can be a mesh netting that is secured to the inner surface to form a pocket.

BRIEF DESCRIPTION OF THE DRAWINGS

Other and further objects, advantages and features of the present invention will be understood by reference to the following.

DESCRIPTION OF THE INVENTION

Figure 1:
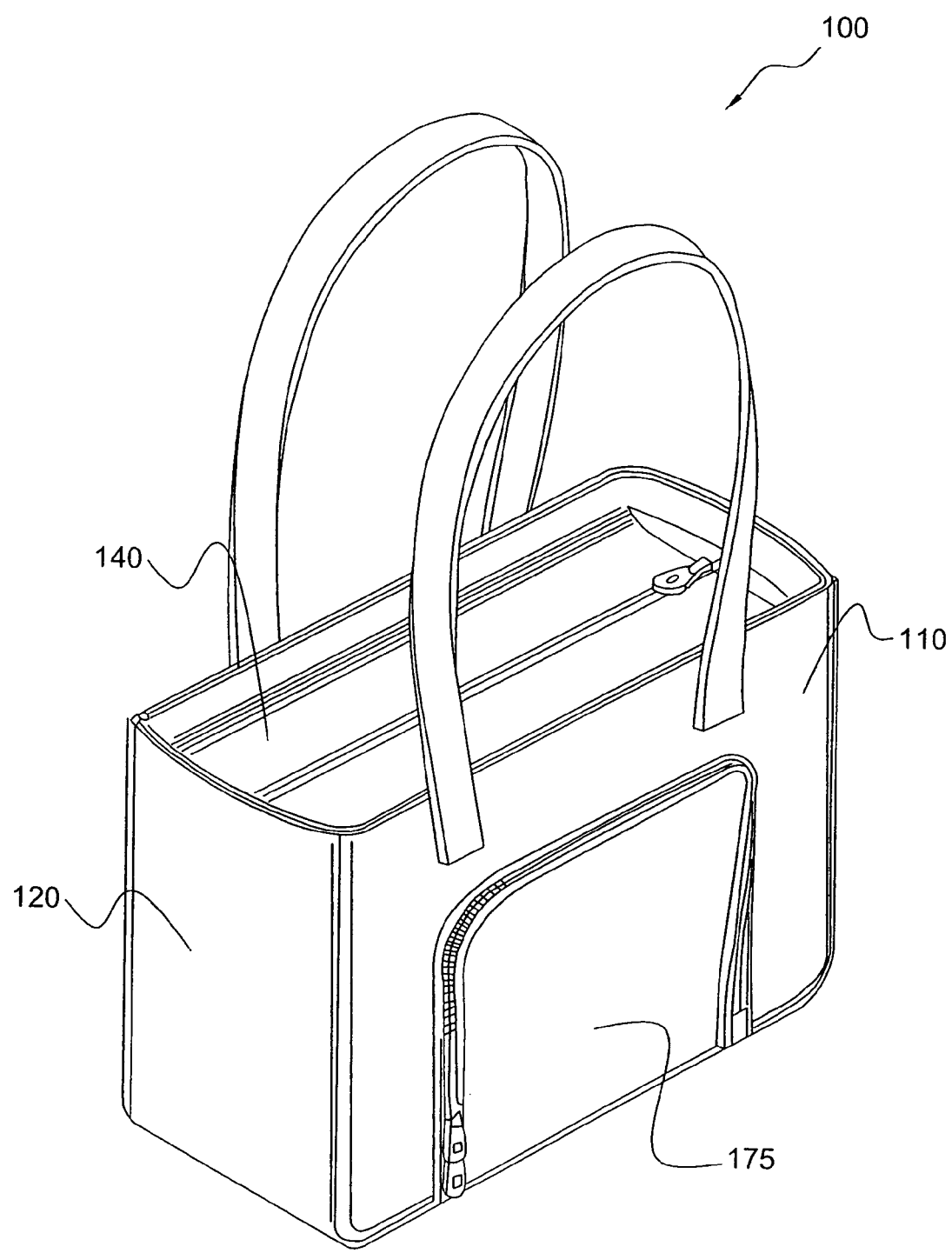
FIG. 1 is a front perspective view of a bag system of the present invention.
Figure 2:
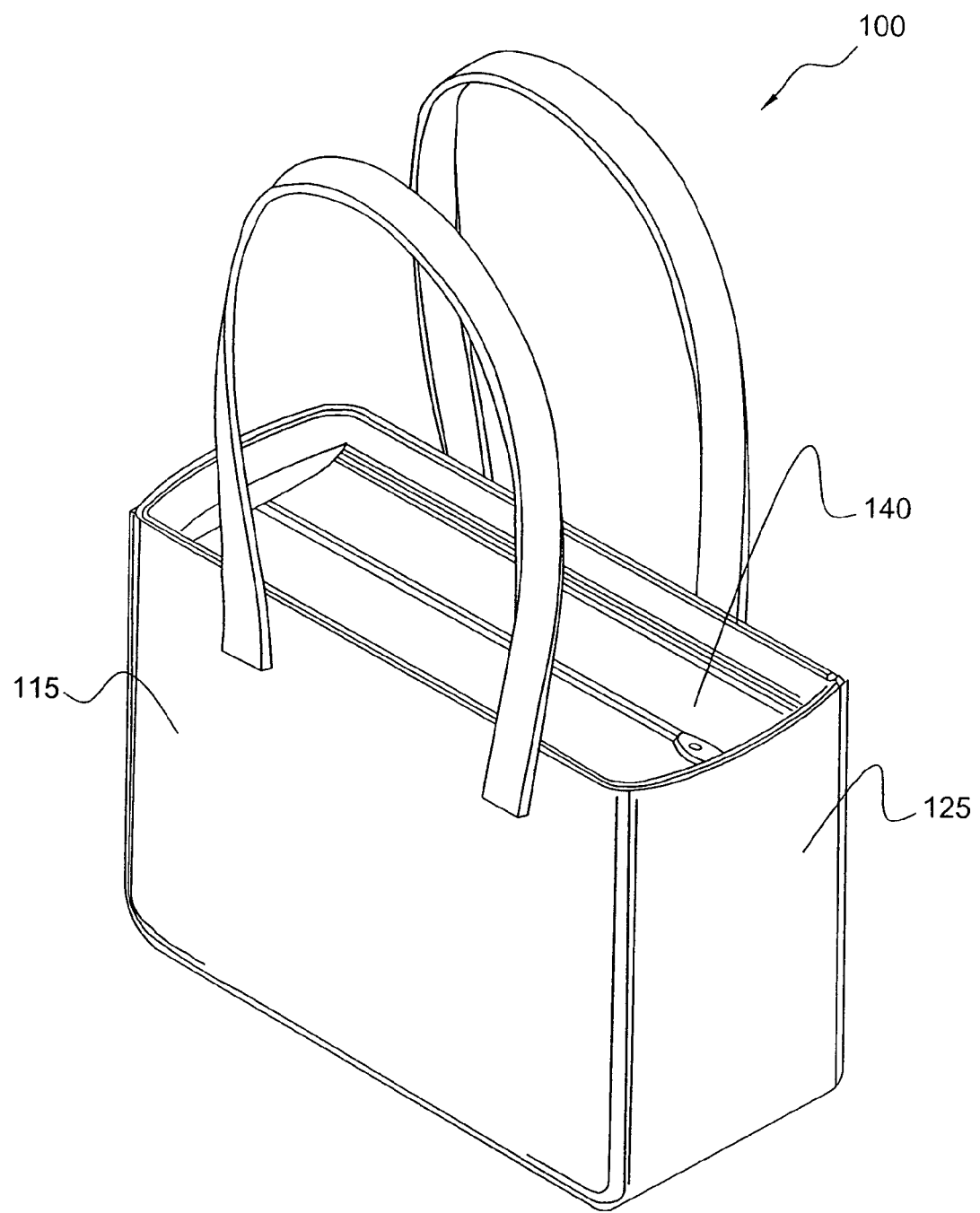
FIG. 2 is a rear perspective view of the bag system of FIG. 1.
Figure 3:
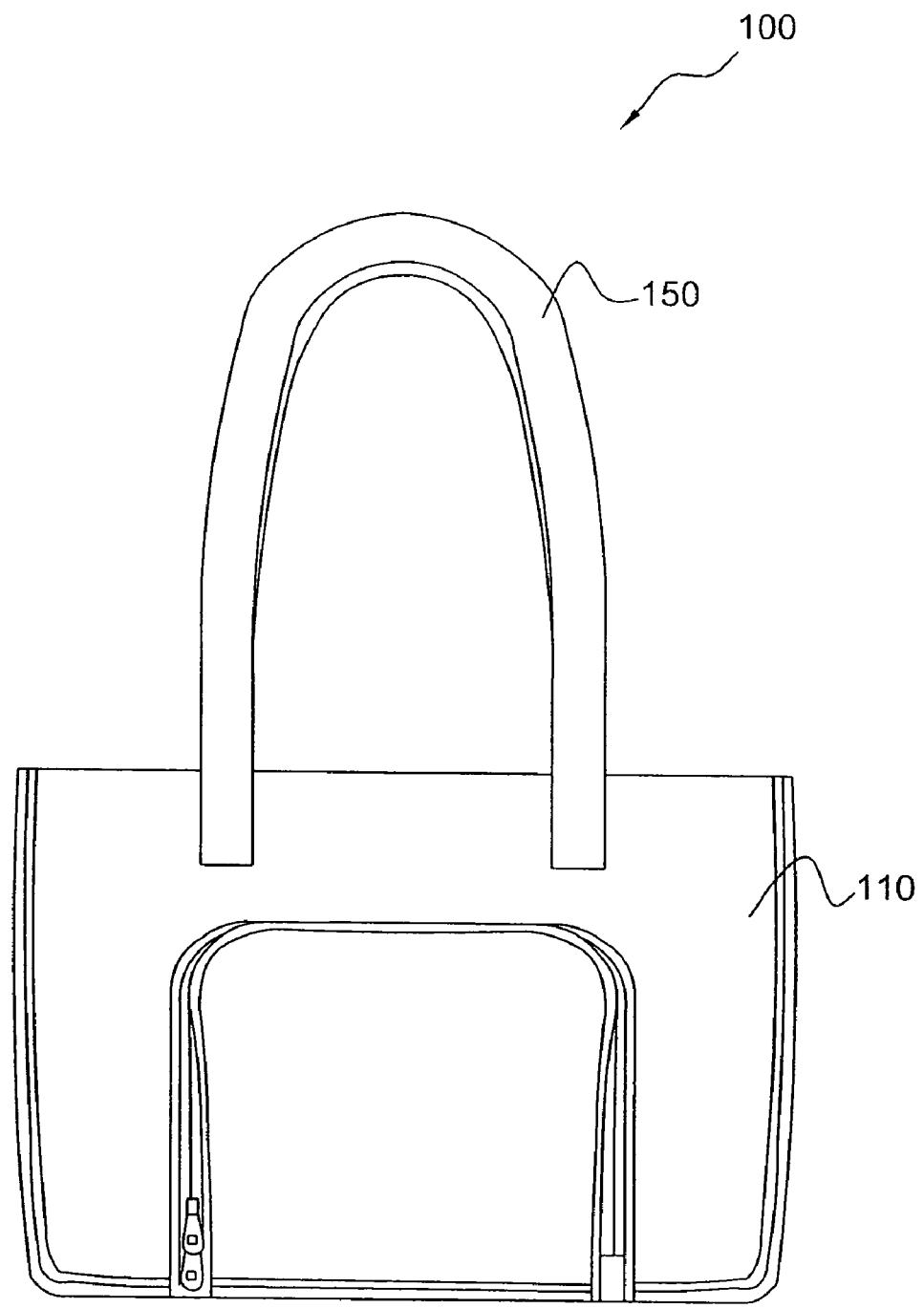
FIG. 3 is a front view of the bag system of FIG. 1.
Figure 4:
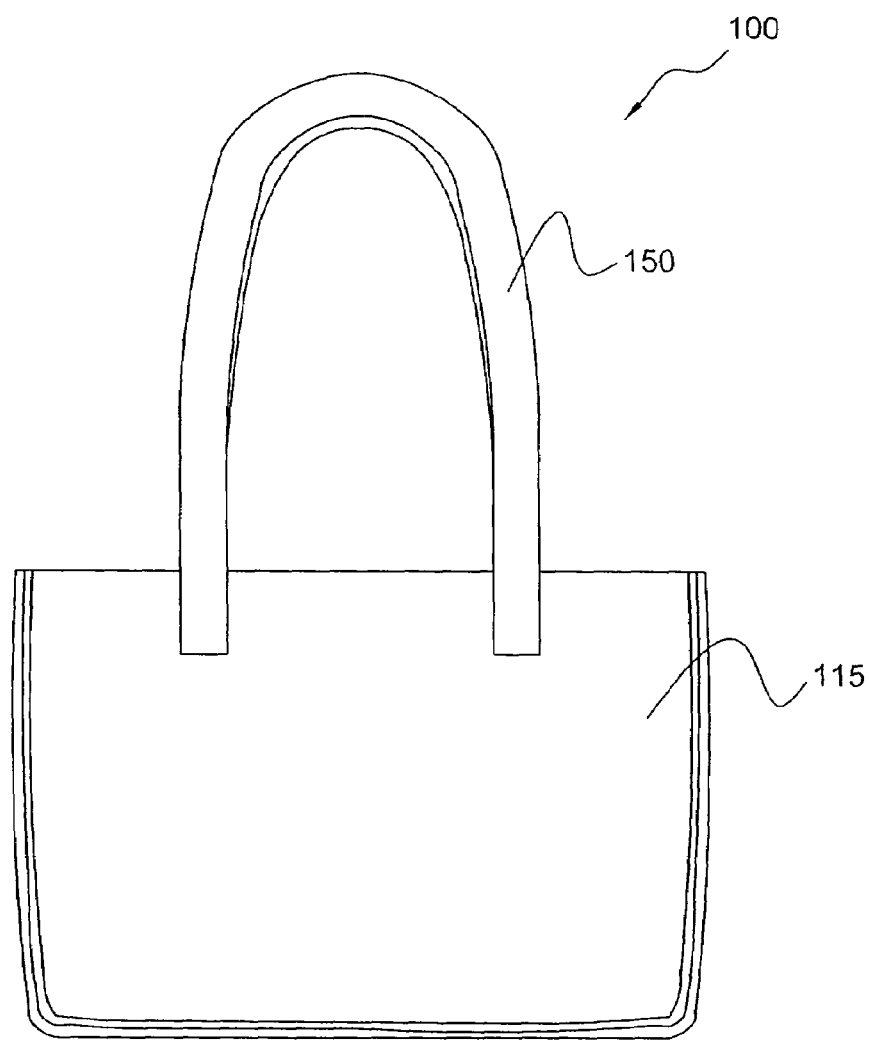
FIG. 4 is a rear view of the bag system of FIG. 1.
Figure 5:
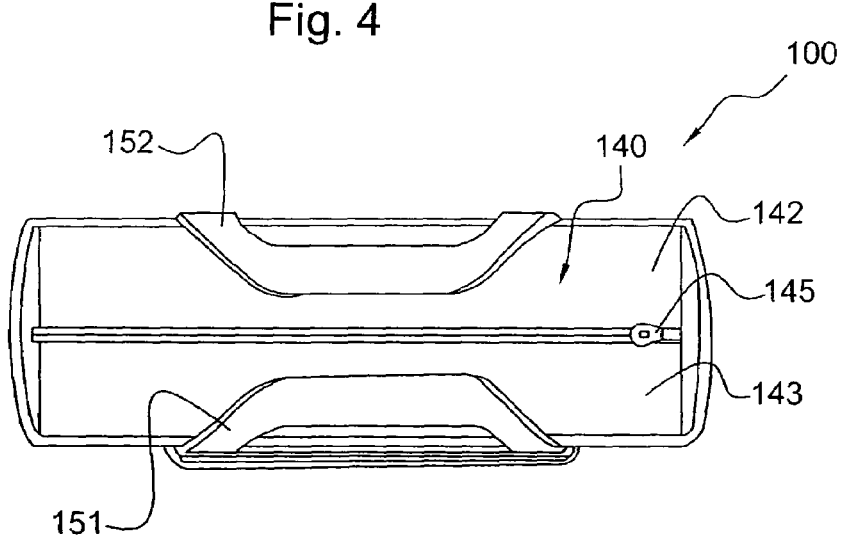
FIG. 5 is a top view of the bag system of FIG. 1.
Figure 6:
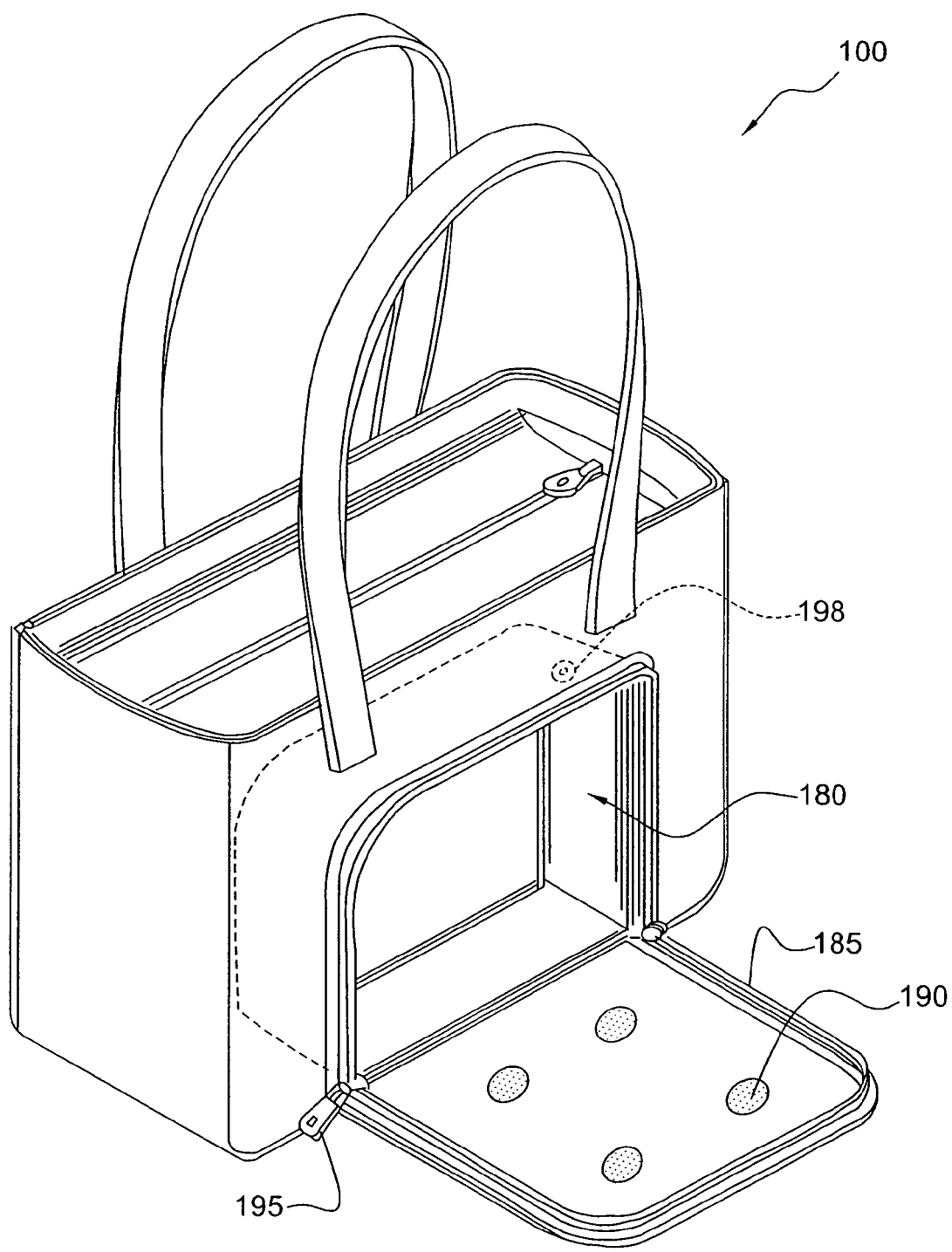
FIG. 6 is a front perspective view of the bag system of FIG. 1 with the front compartment opened.
Figure 6A:
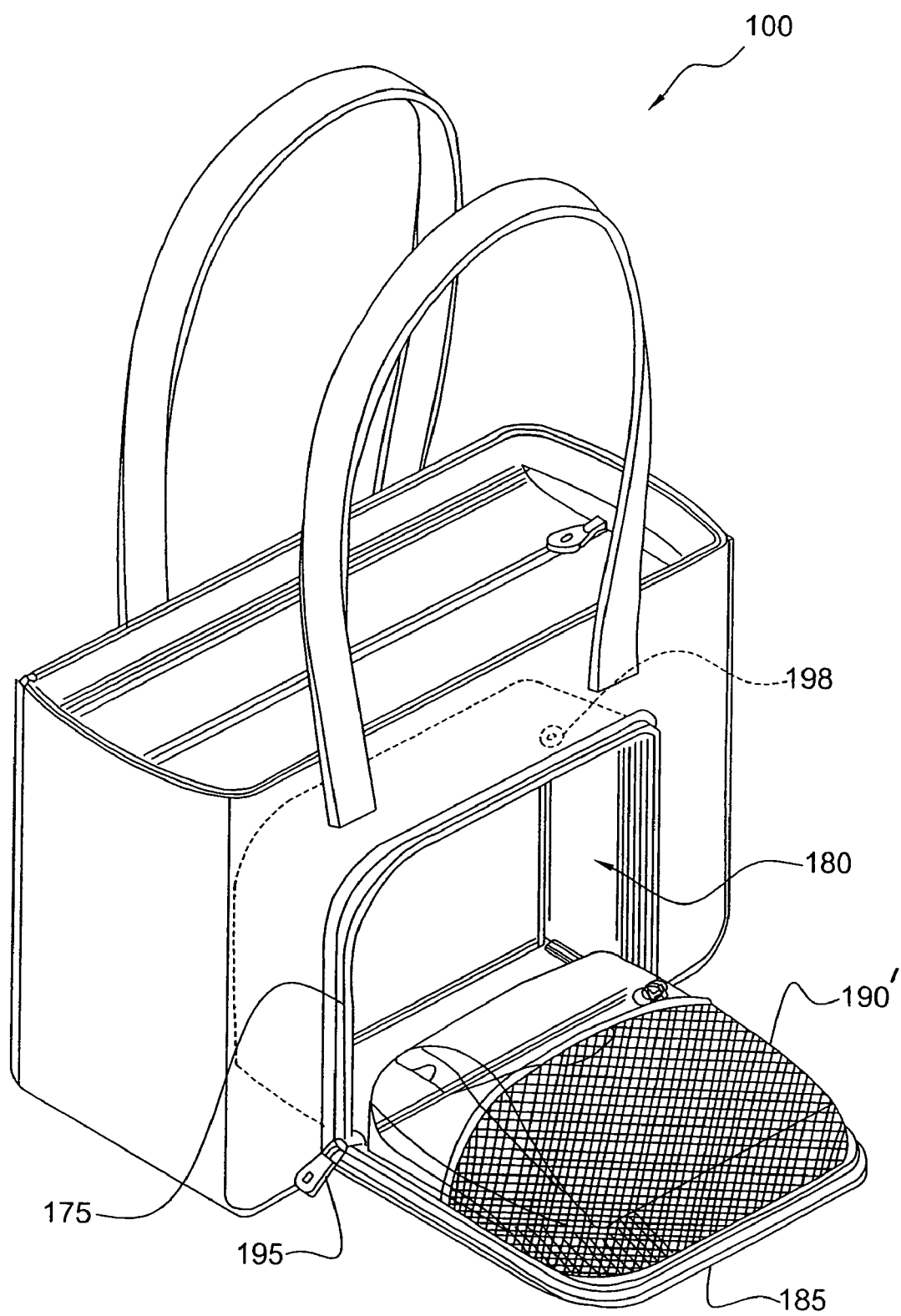
FIG. 6a is a front perspective view of the bag system of FIG. 1 having an alternative embodiment of a holding structure with the front compartment opened and the breast pump stored therein.
Figure 7:
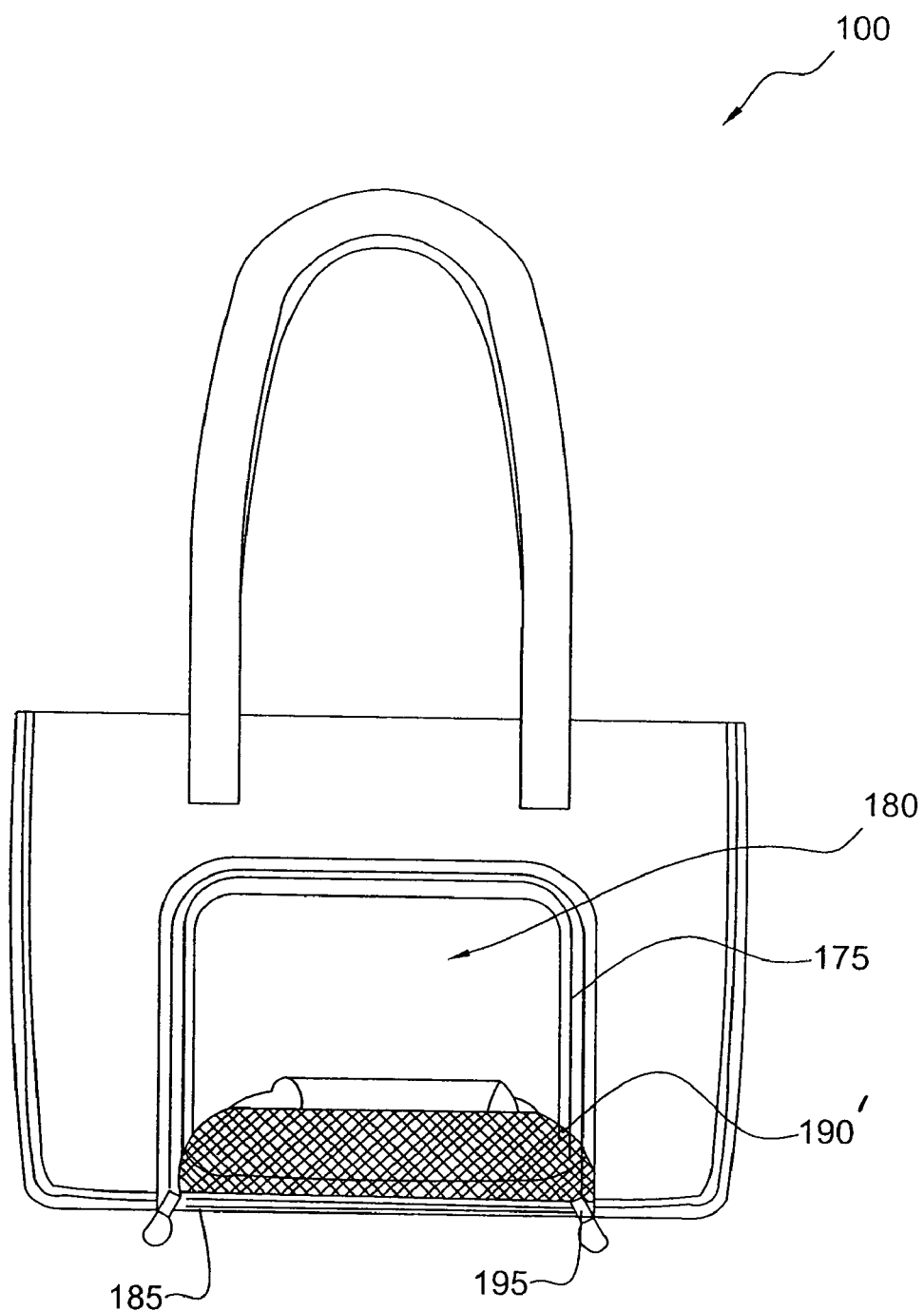
FIG. 7 is a front view of the bag system of FIG. 6a with the front compartment opened and the breast pump stored therein.
Figure 8:
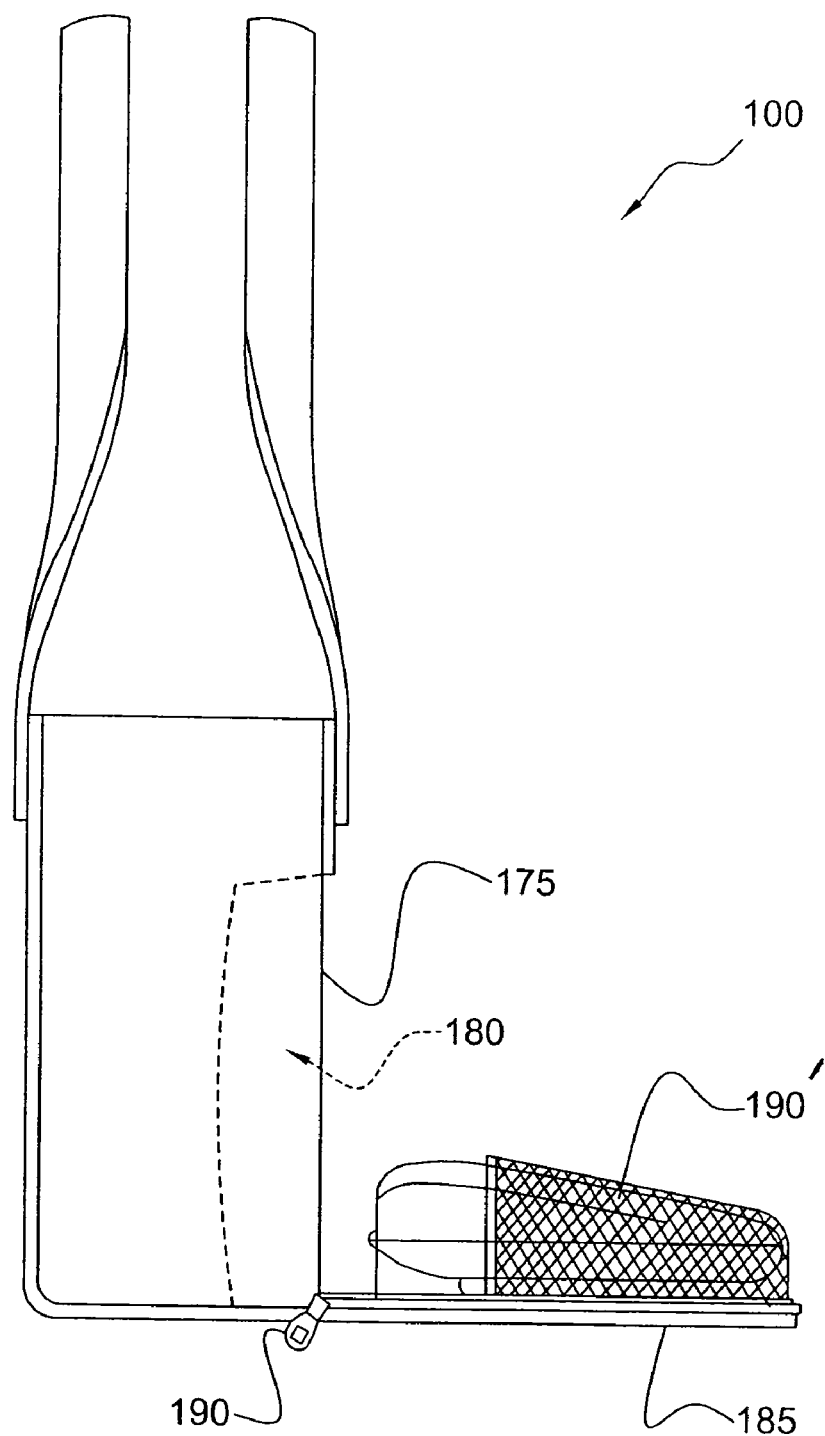
FIG. 8 is a side view of the bag system of FIG. 6a with the front compartment opened and the breast pump stored therein.
Figure 9:
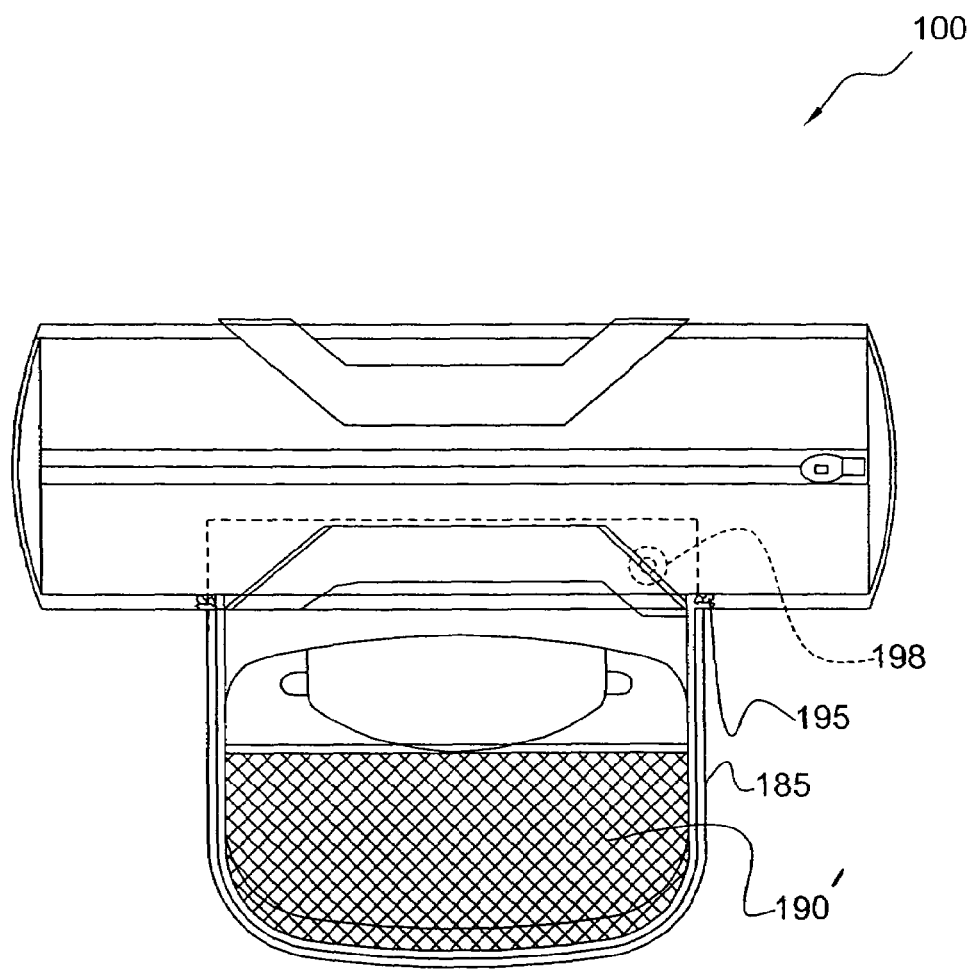
FIG. 9 is a top view of the bag system of FIG. 6a with the front compartment opened and the breast pump stored therein.
Figure 10:
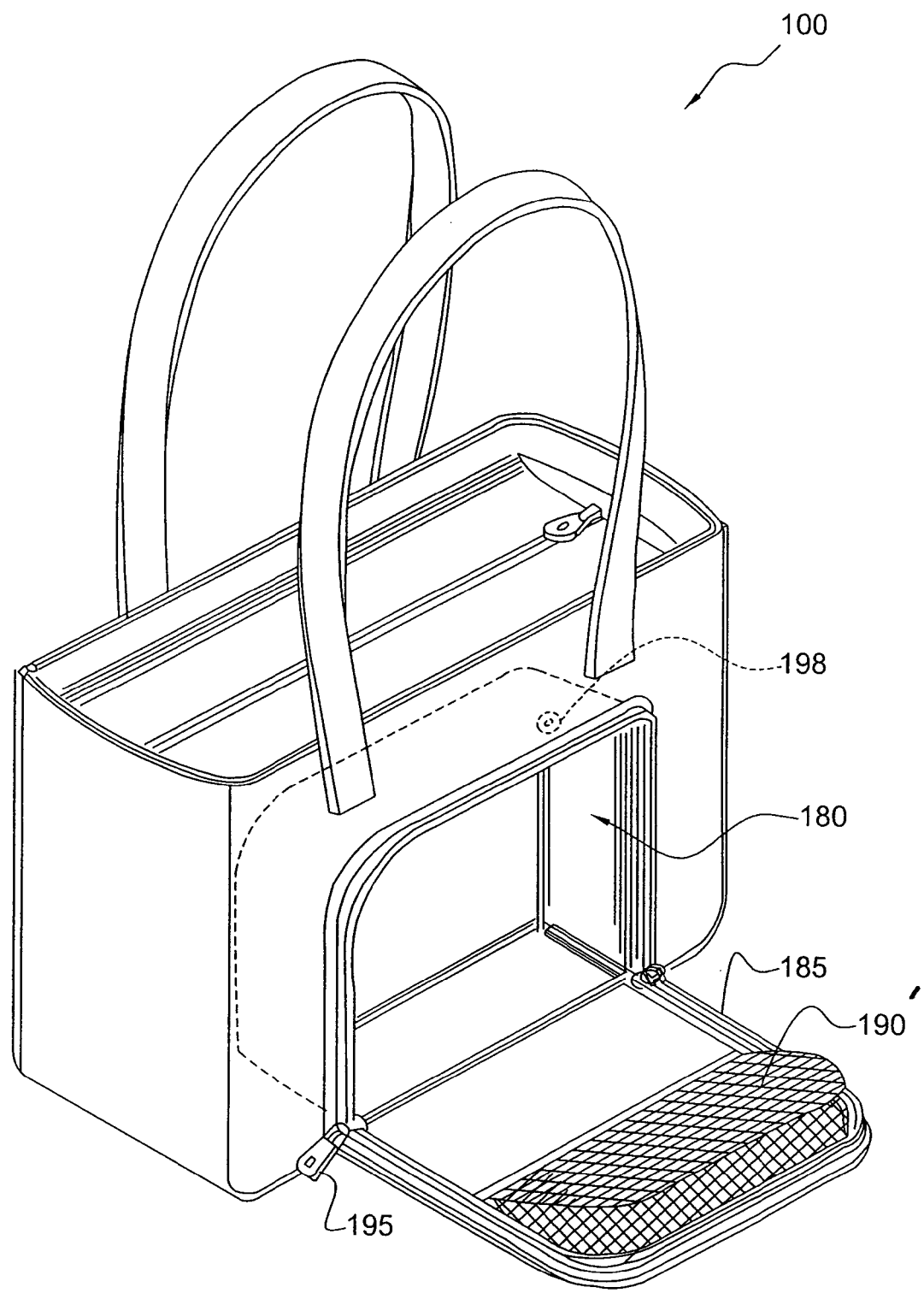
FIG. 10 is a front perspective view of the bag system of FIG. 6a with the front compartment opened.

Referring to the drawings and, in particular, FIG. 1, there is shown a preferred embodiment of a bag of the present invention generally represented by reference numeral 100. Referring to FIGS. 1 and 2, bag 100 has a generally rectangular shape with a front face 110, rear face 115, side walls 120, 125 and a bottom wall (not shown). Front face 110, rear face 115, side walls 120, 125 and the bottom wall are secured to each other to define an inner compartment or volume 130.

Preferably, front face 110, rear face 115, side walls 120, 125 and the bottom wall are stitched together. However, alternative securing methods can also be used, such as, for example, adhesive or an adhesive and stitching combination. Additionally, front face 110, rear face 115, side walls 120, 125 and the bottom wall can be individual panels or can be any combination of panels that are secured together to form bag 100. While the preferred embodiment has a generally rectangular shape, alternative shapes for bag 100 can also be used, such as, for example, triangular or circular.

Referring to FIGS. 1 through 5, the top portion of bag 100 has a closure 140 and a handle 150. Closure 140 is preferably a pair of flaps 142, 143 having a zipper mechanism 145 attached thereto to provide selective access to inner compartment 130. However, alternative fastening structures can also be used for closure 140, such as, for example, buttons, snaps or VELCRO®. Handle 150 is preferably a pair of opposing straps 151, 152 that are secured to the top portions of front face 110 and rear face 115, respectively. Handle 150 preferably has a sufficient length to allow use as a shoulder strap.

Referring to FIGS. 1 through 11, inner compartment 130 has an inner surface 160 with a housing member 165 and a fastening member 170 secured thereto. In this embodiment, housing member 165 is a first and second flexible mesh netting 167, 168, respectively, that is secured to inner surface 160 along the periphery of the netting, leaving a top portion of the periphery of the netting unsecured, such that first and second pockets are formed. Preferably, first and second mesh nettings or pockets 167, 168 are formed on opposing sides of inner surface 160.

Housing member 165 can be used to hold components of the breast pump system, such as, for example, an electrical adaptor. The use of a flexible material for housing member 165, preferably one or more flexible mesh nettings 167, 168, provides the advantages of being able to store different components of varying size in the housing member, providing visibility to the contents of the housing member and facilitating access to inner compartment 130 when the housing member is not in use since the flexible mesh netting 167, 168 will be substantially flat along inner surface 160. However, alternative materials and structures can also be used for housing member 165, such as, for example, a rigid compartment. In this embodiment, two flexible mesh nettings or pockets 167, 168 are provided for housing member 165. However, alternative numbers of housing member 165 can also be used.

Fastening member 170 is a strap or other fastening structure, such as, for example, a hook or VELCRO®, secured to inner surface 160. Preferably, fastening member 170 is a pair of straps or other fastening structures that are disposed on opposing sides of inner surface 160 and on sides adjacent to where housing member 165 is disposed. Fastening member 170 selectively retains additional storage bags within inner volume 130 as will be discussed later in detail.

Front face 110 has a front compartment 175 formed therein. Front compartment 175 has a generally rectangular shape formed by a number of walls with a front volume 180, a front flap 185 having a holding structure 190 secured thereto, a closing structure 195 and a front orifice 198. Front compartment 175 is a separate compartment from inner compartment 130 and is substantially isolated from the inner compartment.

Front compartment 175 selectively houses a breast pump with front volume 180 being large enough to accommodate the breast pump when front flap 185 is closed. An example of such a breast pump, as well as the components of such a system, is disclosed in the co-pending and commonly owned U.S. Application entitled "Breast Pump System" which has been filed evenly herewith, and the disclosure of which is incorporated herein by reference. The separation and substantial isolation of inner compartment 130 and front compartment 175 provides for the additional benefit of separating the breast pump from the other components of the system, e.g., the breast cups and the bottles. An example of such a breast cup is disclosed in the co-pending and commonly owned U.S. Application entitled "Breast Cup" which has been filed evenly herewith, and the disclosure of which is incorporated herein by reference.

Front flap 185 has a generally rectangular shape. Preferably, front flap 185 is integrally formed with front face 110 along a bottom portion or lower periphery of the front flap and is selectively secured to the front face along the remaining portions of the front flap by closing structure 195. More preferably, front flap 185 is integrally formed with front face 110 along a horizontal bottom portion of the periphery of the front flap and is selectively secured to the front face along the side and upper portions of the front flap so that the front flap pivots downwardly and outwardly from bag 100. In an opened position, front flap 185 is preferably in a horizontal position and substantially parallel with the bottom wall of bag 100. In a closed position, front flap 185 is substantially aligned with front face 110 in a common plane or planar section so that the front flap and the front face provide a substantially flat wall.

Holding structure 190 selectively secures the breast pump to front flap 185. Preferably, holding structure 190 is VELCRO® secured to the inner surface of front flap 185 which corresponds to and mates with VELCRO® formed on the bottom surface of the breast pump. More preferably, there are a number of pieces of VELCRO® that make up holding structure 190.

Alternatively, holding structure 190 can be a transparent material such as a flexible mesh netting 190' (shown in FIGS. 6a through 10) having a substantially rectangular shape similar to the shape of front flap 185. This alternative holding structure 190' is secured to the inner surface of front flap 185 along three sides of the netting, leaving a portion or fourth side of the netting unsecured, such that a pocket is formed.

Holding structure 190 is used to removably secure the breast pump to front flap 185, so that when the flap is pivoted away from bag 100 along the bottom periphery of the front flap, the breast pump is accessible and readily useable, i.e., in the proper upright orientation to be used.

The use of VELCRO® on the inside surface of front flap 185 or the flexible mesh netting material for holding structure 190, allows a user to see and use the breast pump and, in particular, to see and use the button control pad and visual indicators or lights on the breast pump in order to operate and control the breast pump while still secured to front flap 185 by holding structure 190. Additionally, the use of the flexible mesh netting for holding structure 190, allows for securing of breast pumps having different shapes and sizes.

Holding structure 190 allows a user to easily insert and remove the breast pump into front compartment 175. Insertion and removal of the breast pump in bag 100 for cleaning purposes is a significant concern to a user. Alternative materials and structures can also be used for holding structure 190, which allow a user to see and use the button control pad and visual indicators, such as, for example, a transparent material, such as, for example, plastic, or one or more flexible or VELCRO® straps.

Closing structure 195 is preferably a zipper mechanism, which runs along the periphery of front flap 185. However, an alternative closing structure 195 can also be used, such as, for example, a hook and loop fastener, such as VELCRO®. Additionally, while this embodiment has front flap 185 that outwardly pivots from bag 100, an alternative front compartment 175 can have a front flap that is selectively removable from the bag so that the breast pump can be completely removed from front compartment 175 while still being retained in holding structure 190.

Front orifice 198 is an opening formed in front compartment 175 that provides communication between front volume 180 and inner compartment 130. Preferably, front orifice 198 is disposed in an upper portion of front compartment 175. Front orifice 198 is preferably a circular opening, which has a diameter large enough for passing an electric cord.

Front orifice 198 allows a user to operate the breast pump while it is disposed on front flap 185 with the electric cord from the breast pump through front volume 180, through the front orifice, through inner compartment 130, and out through closure 140 to a source of power. This provides a user with the option of discrete use of the breast pump since the breast pump will be partially concealed on front flap 185. Alternatively, the breast pump may be removed front flap 185 to operate the breast pump.

Figure 11:
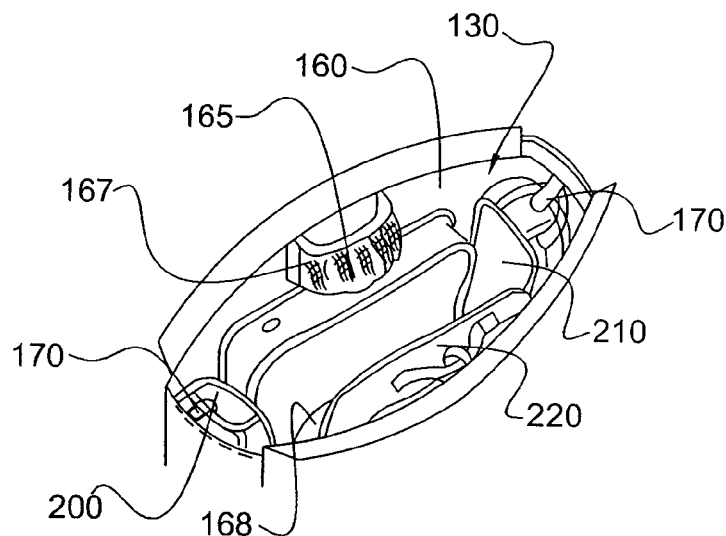
FIG. 11 is a front perspective view of a top portion of the bag system of FIG. 1 with the inner compartment opened.
Figure 12:
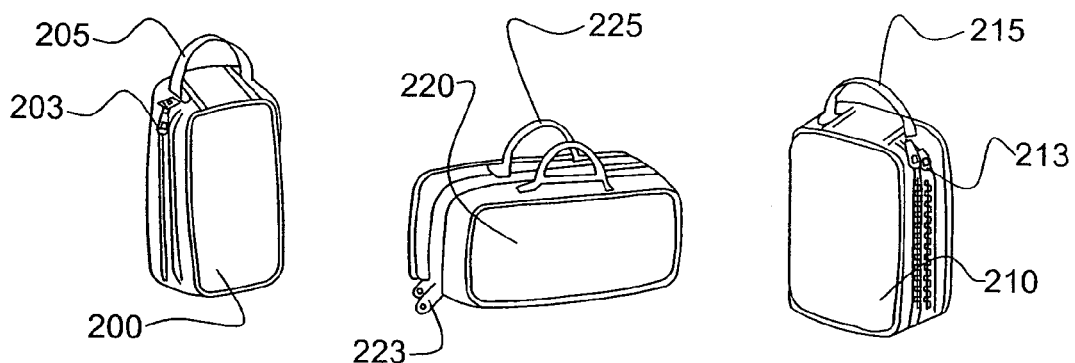
FIG. 12 is a front perspective view of storage bags that can be disposed in the bag system of FIG. 1.
Figure 13:
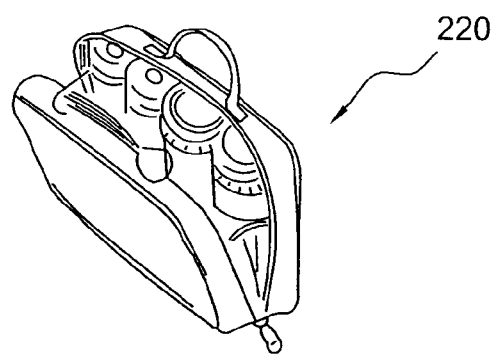
FIG. 13 is a front perspective view of an insulated storage bag of FIG. 12 when opened.

Referring to FIGS. 11 through 13, bag 100 has separate storage bags 200, 210 and 220, which can be disposed in inner compartment 130. Storage bags 200, 210 can be used to store breast cups, bottles or any other components of the breast pump system. By having two separate storage bags 200, 210, a user can separate the used and unused breast cups and bottles in order to avoid or ameliorate contamination of the unused breast cups and bottles. Additionally, the use of storage bags 200, 210, and 220 allow a user to completely remove the bags as opposed to contemporary breast pump bags, which provide a fixed compartment for storage of breast cups and bottles. In this embodiment, there are three separate storage bags 200, 210, and 220. However, any number of storage bags 200, 210, and 220 can be used, which fit within inner compartment 130.

Storage bags 200, 210, and 220 have closures 203, 213 and 223, respectively, and handles 205, 215 and 225, respectively. Preferably, closures 203, 213 and 223 are zipper mechanisms. However, alternative closing mechanisms can also be used for closures 203, 213 and 223, such as, for example, snaps or VELCRO®. Handles 205, 215 and 225 are preferably straps that are secured to a top portion of storage bags 200, 210, and 220, respectively. Storage bags 200 and 210 are preferably disposed on opposing sides of inner compartment 130 with fastening member 170 selectively secured to handles 205, 215 to facilitate retaining the storage bags in the inner compartment.

As shown in FIG. 13, storage bag 220 is preferably a thermally insulated bag, which can store bottles containing breast milk. By having a separate storage bag 220, which is thermally insulated and disposing the breast pump in a separate front compartment 175 that is substantially isolated and/or substantially thermally isolated from inner compartment 130, bag 100 (shown in FIG. 10) provides enhanced thermal isolation for the bottles containing breast milk from sources of heat, i.e., the breast pump. Storage bag 220 is preferably disposed in flexible mesh netting 168 in inner compartment 130.

Figure 14:
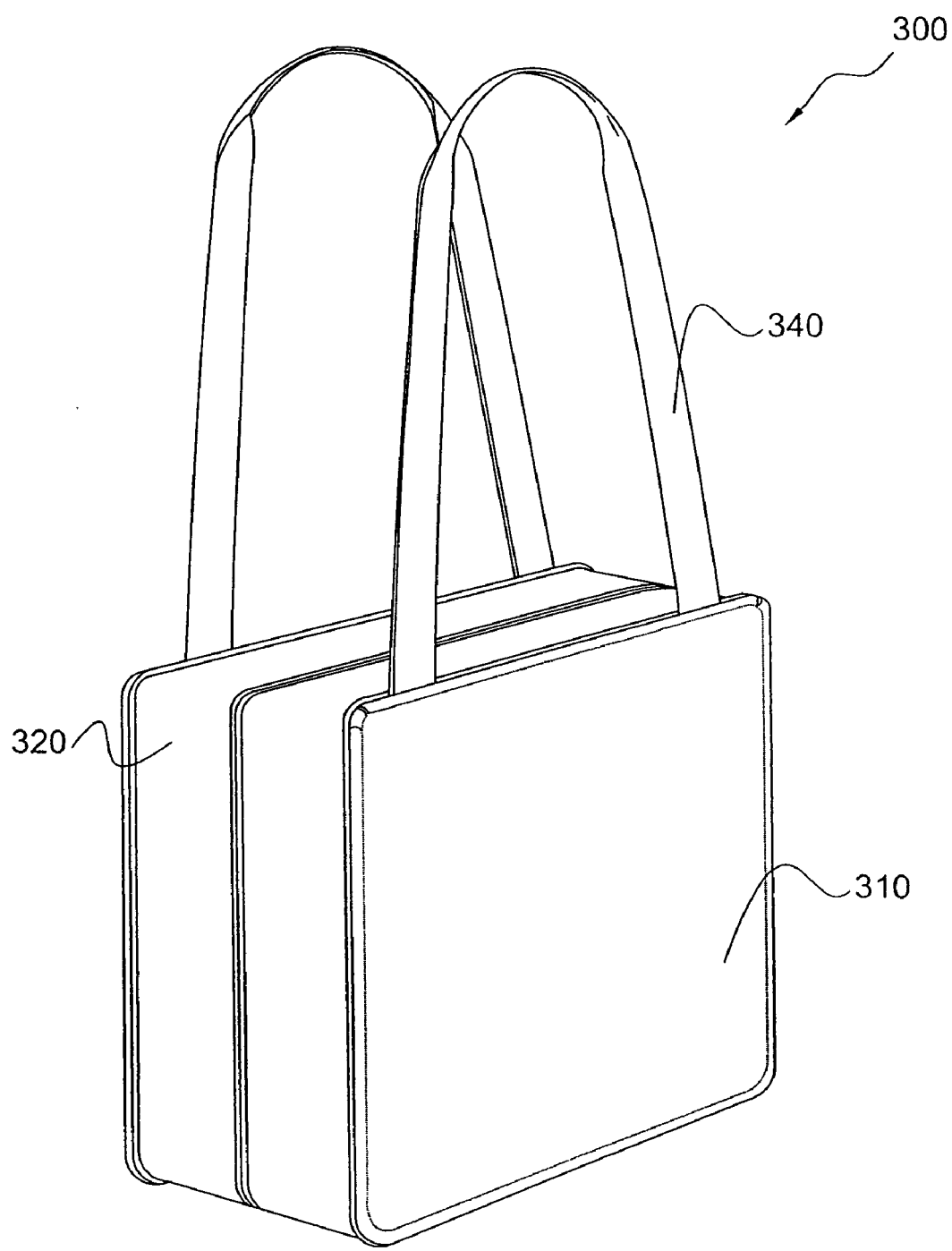
FIG. 14 is a perspective view of an alternative embodiment of the bag system of the present invention.
Figure 15:
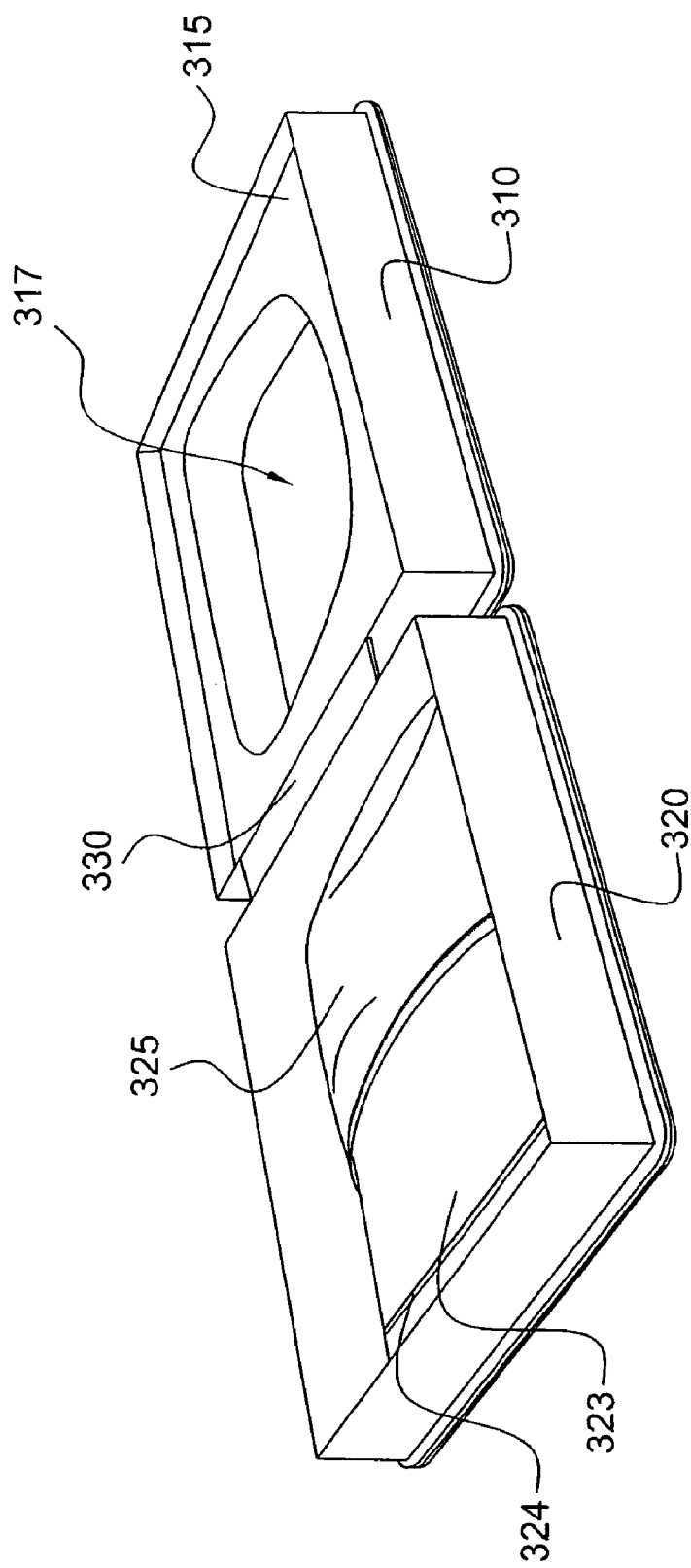
FIG. 15 is a perspective view of the bag system of FIG. 14 when opened.

Referring to FIGS. 14 and 15, there is shown a second embodiment of a bag of the present invention generally represented by reference numeral 300. Bag 300 has a generally rectangular shape with a first portion 310, a second portion 320 and a handle 340. First and second portions 310, 320 are secured at a bottom portion of bag 300 by a hinge 330. In this embodiment, hinge 330 is a flexible fabric hinge. Preferably, first and second portions 310, 320 divide bag 300 in substantially equal halves. Handle 340 is preferably a pair of straps that are shoulder length for use as a shoulder strap. Handle 340 is secured to top portions of first and second portions 310, 320.

First portion 310 has an insert 315 disposed therein. Preferably, insert 315 is a flexible or resilient material such as, for example, foam. Insert 315 has a hollow portion 317 disposed therein. Preferably, hollow portion 317 is substantially centrally located in insert 315. Hollow portion 317 has a shape and size that corresponds to the breast pump. The flexible or resilient material of insert 315 allows a user to more easily insert or remove the breast pump in hollow portion 317. The flexibility of hinge 330 allows bag 300 to be opened to a substantially horizontal position, as shown in FIG. 15. Thus, the breast pump that is disposed in insert 317 will be opened to an accessible and readily useable position, i.e., in the proper upright orientation.

Second portion 320 preferably has a first holding structure 323 and a second holding structure 325. In this embodiment, first holding structure 323 is a flat pocket with a zipper mechanism 324 and second holding structure 325 is an open flexible meshed pocket.

Figure 16:
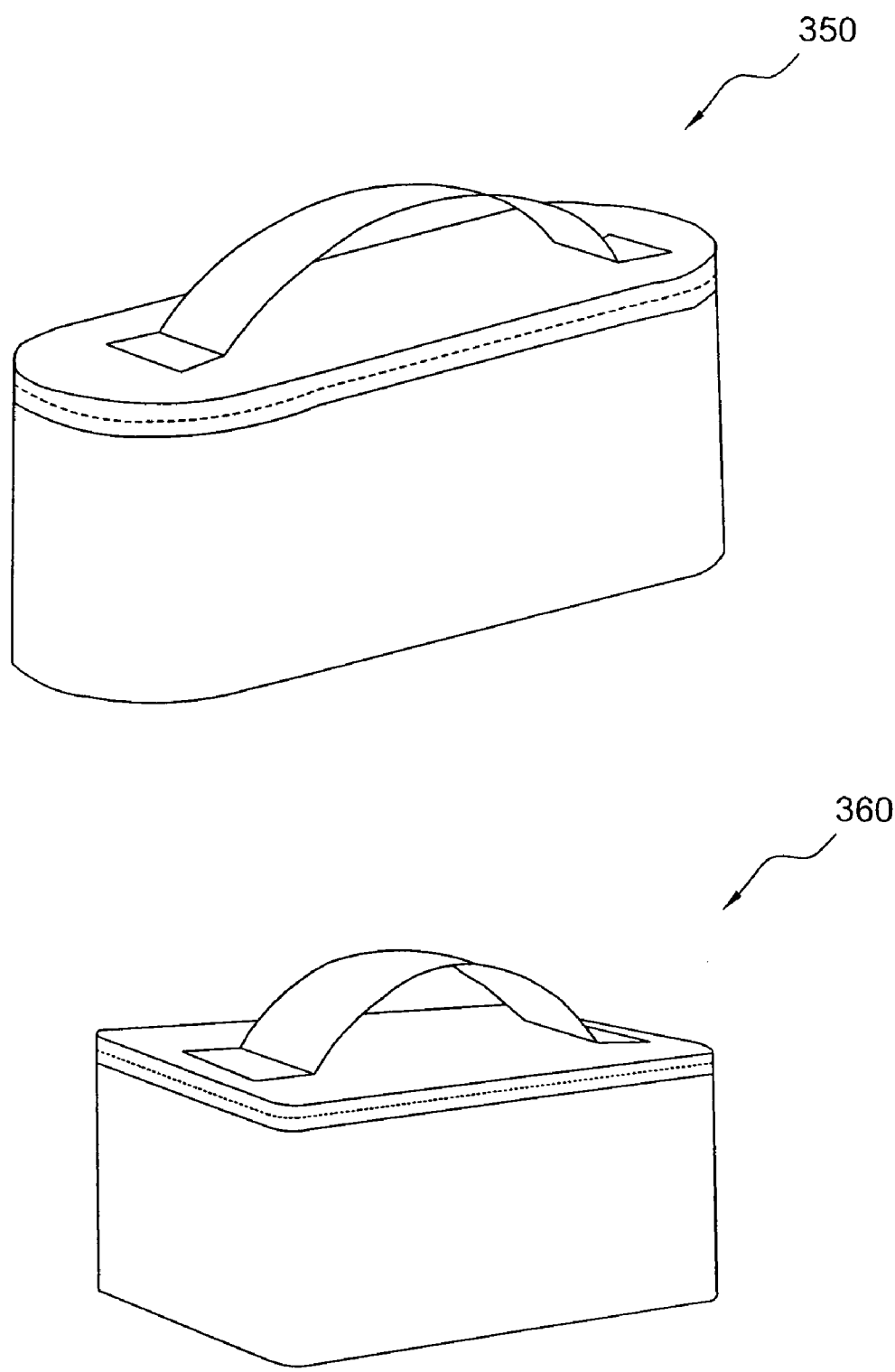
FIG. 16 is a perspective view of inner bags that can be disposed in the bag system of FIG. 14.

Referring to FIGS. 14 through 16, second portion 320 can contain a first inner bag 350 and a second inner bag 360. Inner bags 350, 360 can be used to store breast cups, bottles or any other components of the breast pump system. By having two separate inner bags 350, 360, a user can separate the used and unused breast cups and bottles in order to avoid or ameliorate contamination of the unused breast cups and bottles. Additionally, the use of inner bags 350, 360 allows a user to completely remove the bags as opposed to contemporary breast pump bags, which provide a fixed compartment for storage of breast cups and bottles. Bag 300 can also have an inner liner, which is preferably made with a Poly Vinyl Chloride coating.

Figure 17:
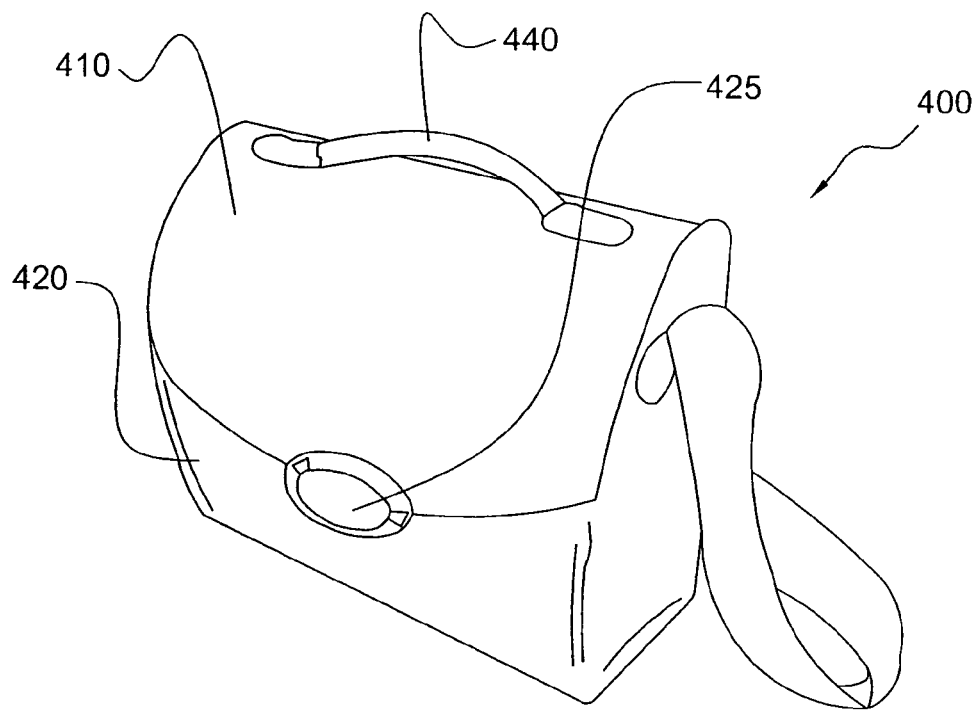
FIG. 17 is a front perspective view of an alternative embodiment of the bag system of the present invention.
Figure 18:
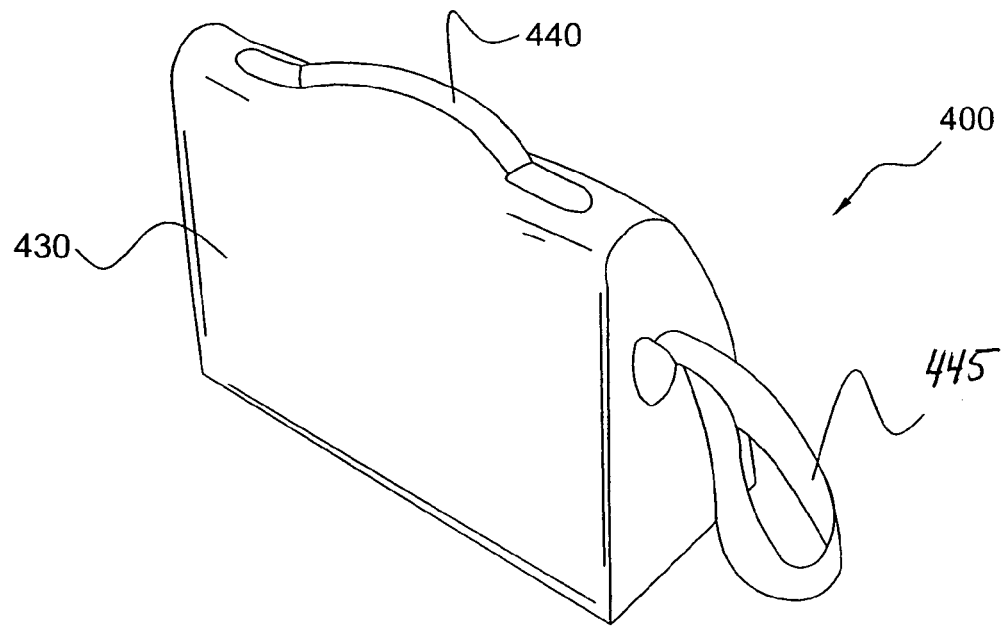
FIG. 18 is a rear perspective view of the bag system of FIG. 17.
Figure 19:
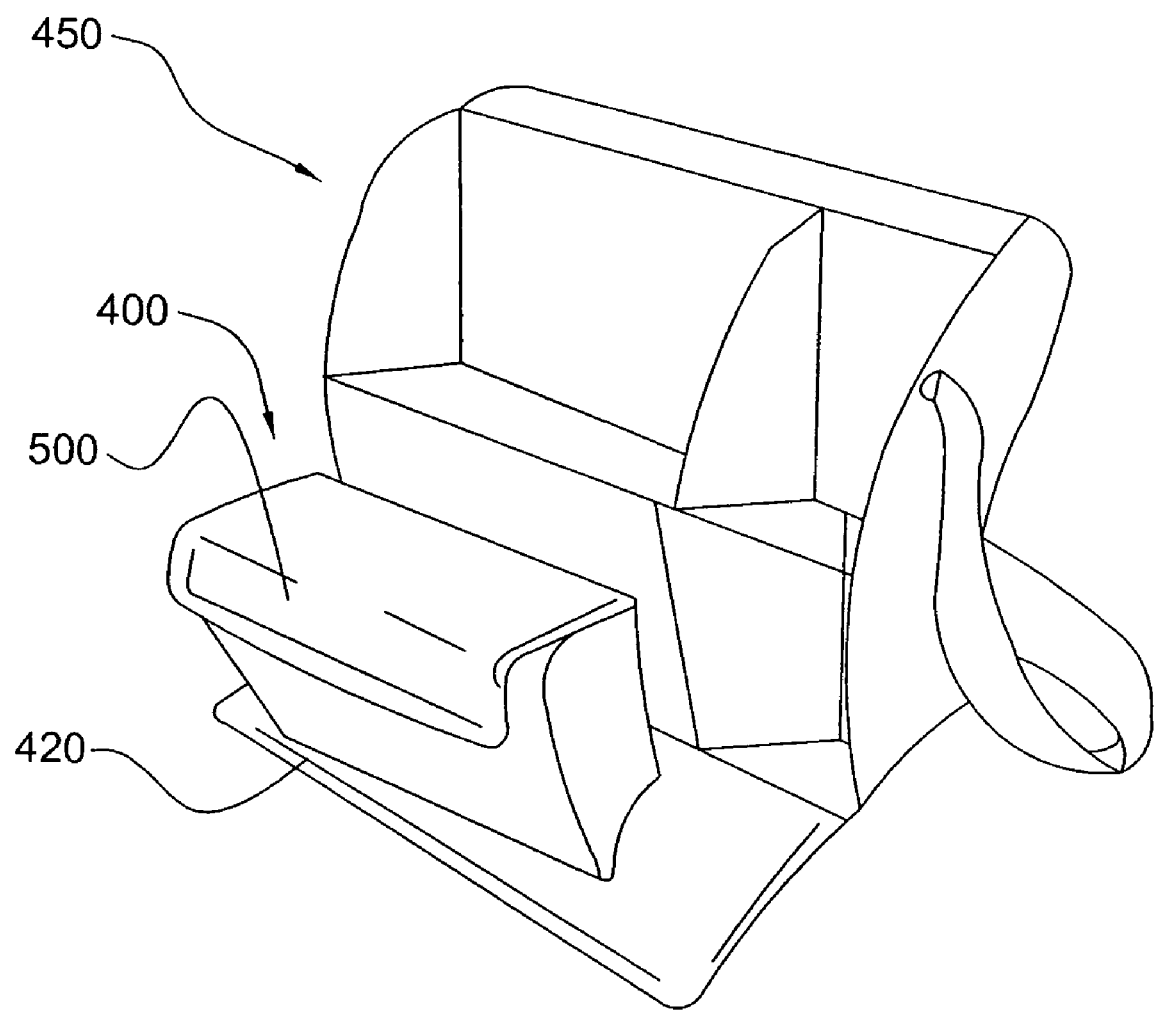
FIG. 19 is a front perspective view of the bag system of FIG. 17 when opened.

Referring to FIGS. 17 through 19, there is shown a third embodiment of a bag of the present invention generally represented by reference numeral 400. Bag 400 has a generally rectangular shape with a top flap 410, a bottom flap 420, a rear wall 430, a handle 440 and a shoulder strap 445.

Top and bottom flaps 410, 420 are secured to rear wall 430 along a portion of the flaps to define an inner volume 450. Preferably, top flap 410 is secured to a top portion of rear wall 430 and bottom flap 420 is secured to a bottom portion of the rear wall so that the top and bottom flaps pivot upwardly and downwardly, respectively, to expose inner volume 450. Bag 400 further has a securing structure 425 that allows a user to selectively secure top flap 410 to bottom flap 420 in order to close the bag. Bag 400 includes both a handle 440 and a shoulder strap 445, which provides a user with options as to how to carry the bag.

Inner volume 450 is compartmentalized to allow a user to separately store the breast pump, breast cups, a thermally insulated bag 500 and other components of the breast pump system, such as, for example, an electrical adaptor. Bag 400 allows a user to use the breast pump inside or outside of the bag and further facilitates accessing the breast pump. Insulated bag 500 allows a user to store bottled breast milk in bag 400.

The present invention having been thus described with particular reference to the preferred forms thereof, it will be obvious that various changes and modifications may be made therein without departing from the spirit and scope of the present invention as defined in the appended claims.

What is claimed is:

1. A bag for a breast pump comprising:
    a plurality of walls;
    a first closure, said plurality of walls and said first closure being operably connected to each other to form a first compartment; and
    a second closure operably connected to at least one of said plurality of walls,
    wherein said second closure is a flap having an inside surface, said flap being pivotally connected to said at least one of said plurality of walls, wherein said inside surface of said flap has a holding structure thereon for removably holding the breast pump on said flap,
    wherein said holding structure supports the breast pump in an operable position on said flap,
    wherein one of said plurality of walls is a front wall, wherein said flap is pivotally connected to said front wall, wherein said flap opens into an open position to access said inside surface, and said flap closes into a closed position so that said front wall and said flap are substantially in a same plane and said flap forms part of said front wall.

2. The bag of claim 1, wherein another of said plurality of walls is a rear wall, said rear wall being opposite to said second closure, and wherein said holding structure remains separated from said rear wall when said flap is pivoted to said closed position.

3. The bag of claim 2, wherein said front wall has a bottom portion, wherein said plurality of walls has a third wall that is a bottom wall, wherein said flap is pivotally connected to said bottom portion of said front wall so that said flap opens into said open position that is substantially adjacent to said bottom wall and substantially parallel with said bottom wall, and wherein said holding structure retains said breast pump on said flap so that said breast pump is in an upright orientation when said flap is in said open position.

4. The bag of claim 2, wherein said holding structure is substantially transparent.

5. The bag of claim 2, wherein said second closure is a zipper.

6. The bag of claim 2, wherein said holding structure is a hook and loop fastener.

7. The bag of claim 2, wherein said holding structure is a mesh netting that is secured to said inside surface of said flap to form a pocket.

8. The bag of claim 7, wherein said mesh netting covers about half of said inside surface of said flap.

9. A bag system for a breast pump system having a breast pump, one or more breast cups and one or more bottles, the bag system comprising:
    an inner bag; and
    an outer bag having:
        a plurality of walls;
        a first closure, said plurality of walls and said first closure being operably connected to form a first compartment; and a second closure operably connected to at least one of said plurality of walls, wherein said second closure is a flap having an inside surface, said flap being pivotally connected to said at least one of said plurality of walls, wherein said inside surface of said flap has a holding structure thereon for removably holding said breast pump in an operable position on said flap and wherein said inner bag has a volume with a size and shape for holding at least one of said one or more breast cups or said one or more bottles, wherein one of said plurality of walls is a front wall, wherein said flap is pivotally connected to said front wall, wherein said flap opens to an open position to access said inside surface, and wherein said flap closes to a closed position so that said front wall and said flap are substantially in a same plane and said flap forms part of said front wall.

10. The bag system of claim 9, wherein another one of said plurality of walls is a rear wall, said rear wall being opposite to said second closure, and wherein said holding structure remains separated from said rear wall when said flap is pivoted into a closed position.

11. The bag system of claim 9, wherein said front wall has a bottom portion, wherein said plurality of walls has a third wall that is a bottom wall, wherein said flap is pivotally connected to said bottom portion of said front wall so that said flap opens into said open position that is substantially adjacent to said bottom wall and substantially parallel with said bottom wall, and wherein said holding structure retains said breast pump on said flap so that said breast pump is in an upright orientation when said flap is in said open position.

12. The bag system of claim 9, wherein said holding structure is substantially transparent.

13. The bag system of claim 9, wherein said holding structure is a mesh netting that is secured to said inside surface of said flap to form a pocket.

14. The bag system of claim 9, wherein said holding structure is a hook and loop fastener.

15. The bag system of claim 9, wherein said inner bag is a plurality of inner bags, and wherein at least one of said plurality of inner bags is thermally insulated.

16. The bag system of claim 9, wherein said first compartment has an inner surface with a fastening member thereon, said fastening member being removably securable to said inner bag to selectively retain said inner bag in said first compartment.

17. The bag system of claim 9, wherein said first compartment has an inner surface with a housing member thereon, said housing member being a mesh netting that is secured to said inner surface to form a pocket.

18. A bag system for a breast pump system having a breast pump, a breast cup and a bottle, the bag system comprising:
   an inner bag having a size and shape to allow for storage of said breast cup or said bottle; and
   an outer bag having:
      a plurality of walls;
      a first closure, said plurality of walls and said first closure being operably connected to form a first compartment; and
      a second closure operably connected to at least one of said plurality of walls to form a second compartment, wherein said second closure is connected to at least one of said plurality of walls so that said second closure opens into an open position, and wherein said breast pump is in an upright orientation when said second closure is in said open position, wherein said second closure is a flap having an inside surface, wherein one of said plurality of walls is a front wall, wherein said flap is pivotally connected to said front wall, wherein said inside surface of said flap has a holding structure thereon for removably holding the breast pump in an operable position on said flap, and wherein said flap opens to the open position to access said second compartment and said flap closes to a closed position so that said front wall and said flap are substantially in a same plane and said flap forms part of said front wall.

* * * * *